United States Patent
Bryant (10) Patent No.: US 7,056,795 B2
(45) Date of Patent: *Jun. 6, 2006

(54) THIN-FILM TRANSISTOR USED AS HEATING ELEMENT FOR MICROREACTION CHAMBER

(75) Inventor: Frank R. Bryant, Denton, TX (US)

(73) Assignee: STMicroelectronics, Inc., Carrollton, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/028,985

(22) Filed: Jan. 3, 2005

(65) Prior Publication Data

US 2005/0136598 A1 Jun. 23, 2005

Related U.S. Application Data

(62) Division of application No. 10/273,690, filed on Oct. 18, 2002, now Pat. No. 6,864,140, which is a division of application No. 10/028,849, filed on Dec. 20, 2001, now Pat. No. 6,504,226.

(51) Int. Cl.
H01L 21/336 (2006.01)

(52) U.S. Cl. .................. 438/292; 257/510

(58) Field of Classification Search ........... 257/510, 257/519, 777; 347/9–24; 438/21, 54, 282, 438/292, 351, 381–385
See application file for complete search history.

(56) References Cited

U.S. PATENT DOCUMENTS

| | | | |
|---|---|---|---|
| 4,412,227 A | 10/1983 | Hamano | 346/76 PH |
| 5,122,473 A | 6/1992 | Mazzali | 437/40 |
| 5,323,030 A | 6/1994 | Koscica et al. | 257/195 |
| 5,681,997 A | 10/1997 | McHale et al. | 73/727 |
| 6,034,410 A | 3/2000 | Chan et al. | 257/510 |
| 6,091,082 A | 7/2000 | Thomas et al. | 257/77 |
| 6,111,280 A | 8/2000 | Gardner et al. | 257/253 |
| 6,573,142 B1 | 6/2003 | Hsieh | 438/266 |
| 2001/0041357 A1 | 11/2001 | Fouillet et al. | 435/91.1 |
| 2002/0017660 A1 | 2/2002 | Villa et al. | 257/216 |

OTHER PUBLICATIONS

Askeland, R. et al., "The Second-Generation Thermal Inkjet Structure," *Hewlett-Packard Journal*, pp. 28-31, Aug. 1988.
Baker, J. et al., "Design and Development of a Color Thermal Inkjet Print Cartridge," *Hewlett-Packard Journal*, pp. 6-15, Aug. 1988.
Buskirk, W. et al., "Development of High-Resolution Thermal Inkjet Printhead," *Hewlett-Packard Journal*, pp. 55-61, Oct. 1988.
Bhaskar, E. et al., "Development of the Thin-Film Structure for the Thinkjet Printhead," *Hewlett-Packard Journal*, pp. 27-32, May 1985.
Muller, R. et al., *Device Electronics for Integrated Circuits 2d ed.*: Silicon Technology, John Wiley & Sons, New York, 1986, p. 96.

*Primary Examiner*—David Nelms
*Assistant Examiner*—Calvin Lee
(74) *Attorney, Agent, or Firm*—David V. Carlson; Lisa K. Jorgenson (57) ABSTRACT

The thin film transistor formed of polycrystalline silicon is positioned adjacent a heat reaction chamber. The gate electrode for the transistor is formed within a silicon substrate and a gate dielectric is positioned over the gate electrode. A pass transistor is coupled to the gate electrode, the pass transistor having a source/drain region in the same semiconductor substrate and positioned adjacent to the gate electrode of the thin film heating transistor. When the pass transistor is enabled, a voltage is applied to the gate electrode which causes the current to flow from the drain to the source of the thin film transistor. The current flow passes through a highly resistive region which generates heat that is transmitted to the heat reaction chamber.

12 Claims, 6 Drawing Sheets

THIN-FILM TRANSISTOR USED AS HEATING ELEMENT FOR MICROREACTION CHAMBER

CROSS-REFERENCE TO RELATED APPLICATION

This application is a divisional of U.S. patent application Ser. No. 10/273,690, filed Oct. 18, 2002, now pending; which is a divisional of issued U.S. Pat. No. 6,504,226, issued Jan. 7, 2003, which applications are incorporated herein by reference in their entirety.

BACKGROUND OF THE INVENTION

1. Field of the Invention

The present invention relates to a heater for a microreaction chamber and in particular, to use of a thin-film transistor as the heating element in the microreaction chamber and method of making the same.

2. Description of the Related Art

The treatment of some fluids, whether liquid or gas, involves an increasingly precise temperature regulation. It is frequently necessary to have very small amounts of fluid be rapidly elevated to a particular temperature under precise controls.

Current inkjet technology relies on placing a small amount of ink within an ink chamber, rapidly heating the ink and ejecting it to provide an ink drop at a selected location on an adjacent surface, such as a sheet of paper. Traditionally, ohmic resistors which heat up rapidly when current is passed therethrough have been used to provide the necessary temperature increase of the ink. See, for example, a detailed discussion of ink ejection in an article titled "Thermodynamics and Hydrodynamics of Thermal Ink Jets," by Allen et al., *Hewlett-Packard Journal*, May 1985, pp. 20–27, incorporated herein by reference.

DNA amplification processes also rely on precise temperature control in the various phases. During various phases of the DNA amplification process, the fluid is required to undergo a number of thermal cycles. As the DNA based fluid undergoes a number of cycles of being repeatedly heated and cooled within a selected temperature range, certain biological processes are carried out.

Microheater heaters are also used for optical switching based on a vapor bubble formation to deflect a light beam, optical switching of liquid crystals, and repeated heating of a biological fluid for decomposition detection of bioorganic compounds.

In each of the above instances in use to date, an ohmic resistor through which a current is passed is used as the heating element.

These devices comprise a semiconductor material body accommodating buried channels that are connected, via an input trench and an output trench, to an input reservoir and an output reservoir, respectively, to which the fluid to be processed is supplied, and from which the fluid is collected at the end of the reaction. Above the buried channels, heating elements and thermal sensors are provided to control the thermal conditions of the reaction (which generally requires different temperature cycles, with accurate control of the latter), and, in the output reservoir, detection electrodes are provided for examining the reacted fluid. The heat is generated by supplying electric current to a metal heating element formed on a wafer comprising a semiconductor body with contact regions in electrical contact with the two opposite ends of the heating element and connected to a drive transistor, typically a MOSFET formed on the same wafer.

Microchips are highly suited for miniaturized heater applications. Generally, present techniques for generating local heating in a microchip are based on ohmic resistors made of metal alloys, such as TaAl, HfB, ternary alloys, etc., or polycrystalline semiconductors. The heating resistor is driven by external circuitry or an integrated power MOSFET. In existing applications, such as thermal inkjet printers, the heating resistor value is preferably higher than the MOSFET channel resistance ($R_{ON}$ or $R_{DS}$) to minimize the parasitic effects and dissipate power in the heating resistor only. Normally, each power MOSFET occupies a large percentage of the chip area to minimize its $R_{ON}$.

At present, various techniques allow thermal control of chemical or biochemical reagents. In particular, from the end of the 1980s, miniaturized devices were developed, and thus had a reduced thermal mass, which could reduce the times necessary to complete the DNA amplification process. Recently, monolithic integrated devices of semiconductor material have been proposed, able to process small fluid quantities with a controlled reaction, and at a low cost (see, for example, U.S. patent application Ser. No. 09/779,980, filed on Feb. 8, 2001; Ser. No. 09/874,382 filed on Jun. 4, 2001; and Ser. No. 09/965,128, filed Sep. 26, 2001; all assigned to STMicroelectronics, S.r.l. and incorporated herein by reference).

One drawback with this arrangement is that the resistance of such ohmic resistors is fixed and cannot be modulated, thus limiting their flexibility. Other drawbacks are that ohmic resistors are subject to material degradation (such as oxidation, segregation, etc.), and electromigration, especially at high temperatures. These phenomena limit their lifetime and are a concern for the reliability of devices that incorporate them into their design.

Yet another drawback is power control. Ohmic resistors, which are either current or voltage driven, dissipate a power that is a quadratic function of the parameters. This results in poor control over their output, as small variations in current or voltage can cause significant fluctuations in power and temperature output.

The present invention provides a miniaturized heater that provides the desired characteristics for many microfluidic and micromechanical applications, while overcoming the drawbacks noted above, while providing other related advantages.

BRIEF SUMMARY OF THE INVENTION

According to principles of the present invention, a thin-film transistor is used as the heating element for a microreaction chamber. The channel of the thin-film transistor is used as the heat element. The current passing through the channel raises the temperature of the channel itself to an elevated level. The channel material as well as its size and properties are selected so that it has a known and desired temperature response for to current passing therethrough. The gate voltage, and thus the amount of current is selected to provide a desired heat response to elevate the temperature of the channel region itself and thus heat any adjacent structures, such as a microreaction chamber.

The thin-film transistor includes a channel region which is formed above a semiconductor substrate and separated therefrom by a dielectric layer. The source and drain are contiguous with and directly connected to the channel layer and are also positioned above the semiconductor substrate.

The gate electrode is positioned within the semiconductor substrate and adjacent the channel region. Placing a selected voltage on the gate electrode causes current to run through the channel region of a desired amount, providing a desired temperature increase. A microreaction chamber is positioned adjacent the channel region so as the channel region temperature increases, the microreaction chamber is heated.

According to one embodiment, an electrically insulating layer is positioned over the channel region to electrically separate the channel region from the microreaction chamber. In an alternative embodiment, the dielectric layer is not needed and the channel region itself is directly exposed within the microreaction chamber.

The microreaction chamber is formed from a layer of material which can easily be etched or micromachined. For example, the microreaction chamber may be comprised of an organic polymer material. In one embodiment, the microreaction chamber has a lid on the top thereof so as to provide an enclosure for the heat responsive reaction chamber.

DETAILED DESCRIPTION OF THE INVENTION

Figure 1:
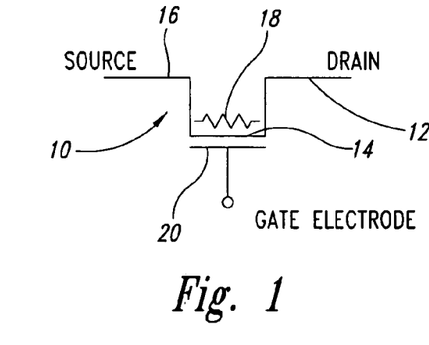
FIG. 1 is an electrical schematic of the thin-film transistor heating element.

FIG. 1 is an electrical schematic of a thin-film transistor 10 which provides the heating element for a heater assembly according to principles of the present invention. The transistor 10 includes a drain region 12, a channel region 14, and a source region 16. Within the channel region 14 is a resistive element 18 which heats up in response to a current passing from the drain to the source. Adjacent the channel region 14 is a gate electrode 20. When a voltage is placed on the gate electrode 20, the transistor 10 is enabled so that a current may pass from the drain to the source via the channel region 14 and thus heat a resistive region within the channel region to a desired temperature.

Figure 2:
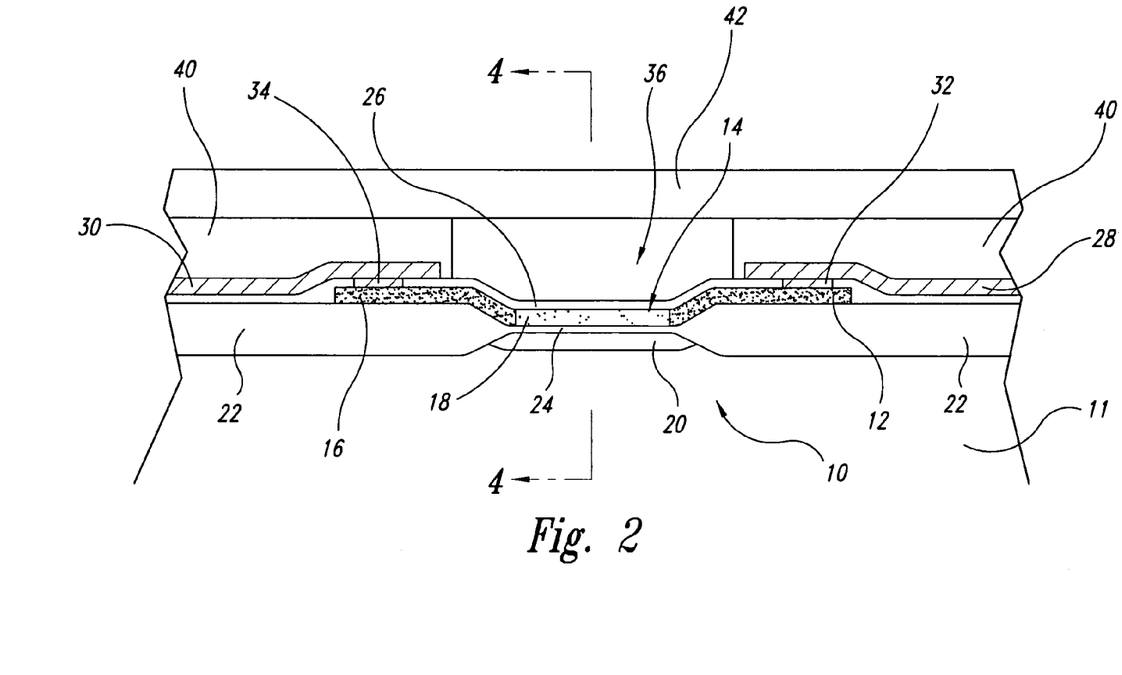
FIG. 2 is a cross-sectional view of the heater assembly, taken along lines 2—2 of FIG. 3.

FIG. 2 is a cross-sectional view of one embodiment of the thin-film transistor semiconductor heater assembly. A semiconductor substrate 11 is lightly doped having a desired conductivity type, and may be either a p-type or n-type depending on the desired configuration. Within the semiconductor region 11, an active area is defined between appropriate insulation regions 22. The insulation regions 22 can be comprised of a trench, a field oxide, trench isolation filled with a dielectric or any acceptable material 22 as is known in the art. Within the active area a gate electrode 20 is formed by implanting a high concentration of a dopant material. The dopant material will be opposite the conductivity type of the substrate and can be either n-type or p-type. The gate is formed by conventional dopant implantation techniques and may be formed prior to the formation of the electrical isolation regions 22 or after, depending on the process used. On top of the gate electrode 20 is formed a gate dielectric 24. The gate dielectric 24 may be a silicon dioxide, a silicon nitride, a sandwich layer of silicon dioxide/silicon nitride or some other combination of dielectric material suitable for forming a gate dielectric. A polysilicon layer is formed over the gate dielectric 24 and extends as a contiguous single layer over the electrical isolation region 22. The polysilicon layer is doped at either end to form a drain region 12 and a source region 16. A central region 14 is to become the channel region of the thin-film transistor 10. The source and drain are heavily doped with the appropriate conductivity type depending on the type of transistor to be formed. For example, it may be heavily doped with boron to form a p-channel transistor or, alternatively, with phosphorous and/or arsenic for an n-channel device. The channel region 14 is lightly doped of the appropriate conductivity type so as to provide a high resistance region which heats to a significant temperature when a current is passed therethrough. The channel region 14 is preferably doped with the opposite conductivity as the source and drain, for example if the source and drain are doped n-type then the channel region is doped p-type, and vice versa.

The thin-film transistor is composed of polycrystalline silicon which has unusual properties when lightly doped. In some instances, undoped or very lightly doped polycrystalline silicon behaves as p-type material. Therefore, in one embodiment the channel region 14 is undoped polycrystalline silicon, and the apparent p-type conductive properties are utilized in the thin-film transistor. It may also be lightly doped p-type or n-type in order to form the desired resistive region 18 and a channel having the desired threshold. The channel doping may be the same or opposite that of the source and drain. Since the material is polysilicon, the electrical response to various doping levels will be different from that of monocrystalline silicon, as is published in many well-known literature sources.

Over the thin-film transistor 10 is formed a passivation layer 26. The passivation layer 26 may be selected for its thermal properties as well as for its electrical insulation properties. For example, it may be a silicon dioxide, silicon nitride, or other material which is an electrical insulator and has relatively stable thermal characteristics. Alternatively, it may be a silicon carbide, which is a dielectric but is more thermally conductive than a silicon dioxide or silicon nitride. Other materials may also be selected which may not be dielectric layers but which are highly thermally conductive and inert to the fluid in the chamber. These may include a tantalum alloy, aluminum, or some other passivation layer. The purpose of passivation layer 26 is to provide protection to the transistor 10 so that, as different materials enter the reaction chamber, the operation of transistor 10 is not degraded.

A highly conductive wiring line 28 is coupled to the drain 12 and a highly conductive wiring line 30 is connected to the source 16. Preferably the wiring lines 28 and 30 are composed of a metallic layer, such as aluminum, copper, titanium, tungsten or some alloy therefor. The wiring layers 28 and 30 are coupled to the source and drain by the appropriate contacts 32 and 34 respectively. The contacts 32 and 34 may be tungsten, aluminum, a titanium barrier followed by tungsten, or any other acceptable contact between the wiring layers 28 and 30 and the underlying polycrystalline silicon.

Over the thin-film transistor 10, a heat reaction chamber 36 is formed. The heat reaction chamber 36 is formed by the walls of an appropriate dielectric layer 40 which is formed on top of the source and drain electrodes and appropriately etched. The chamber walls 40 may be composed of any acceptable dielectric material, such as silicon dioxide, silicon nitride, a high density silicon dioxide such as TEOS. In a preferred embodiment, the chamber walls 40 are formed of an organic polymer material which is compatible with the process of the transistor forming sequence. The organic polymer material may be any acceptable organic polymer and in one embodiment a commercially available material known as SU8 is used, while in an alternative embodiment, a photosensitive polyimide is used. A lid 42 is formed over the top of the heater reaction chamber 36. The lid 42 may be formed of the same material and in the same process step as the chamber walls 40. Alternatively, it may be formed in a separate process step, and be of a separate material than the heat chamber material, as explained later herein.

Figure 3:
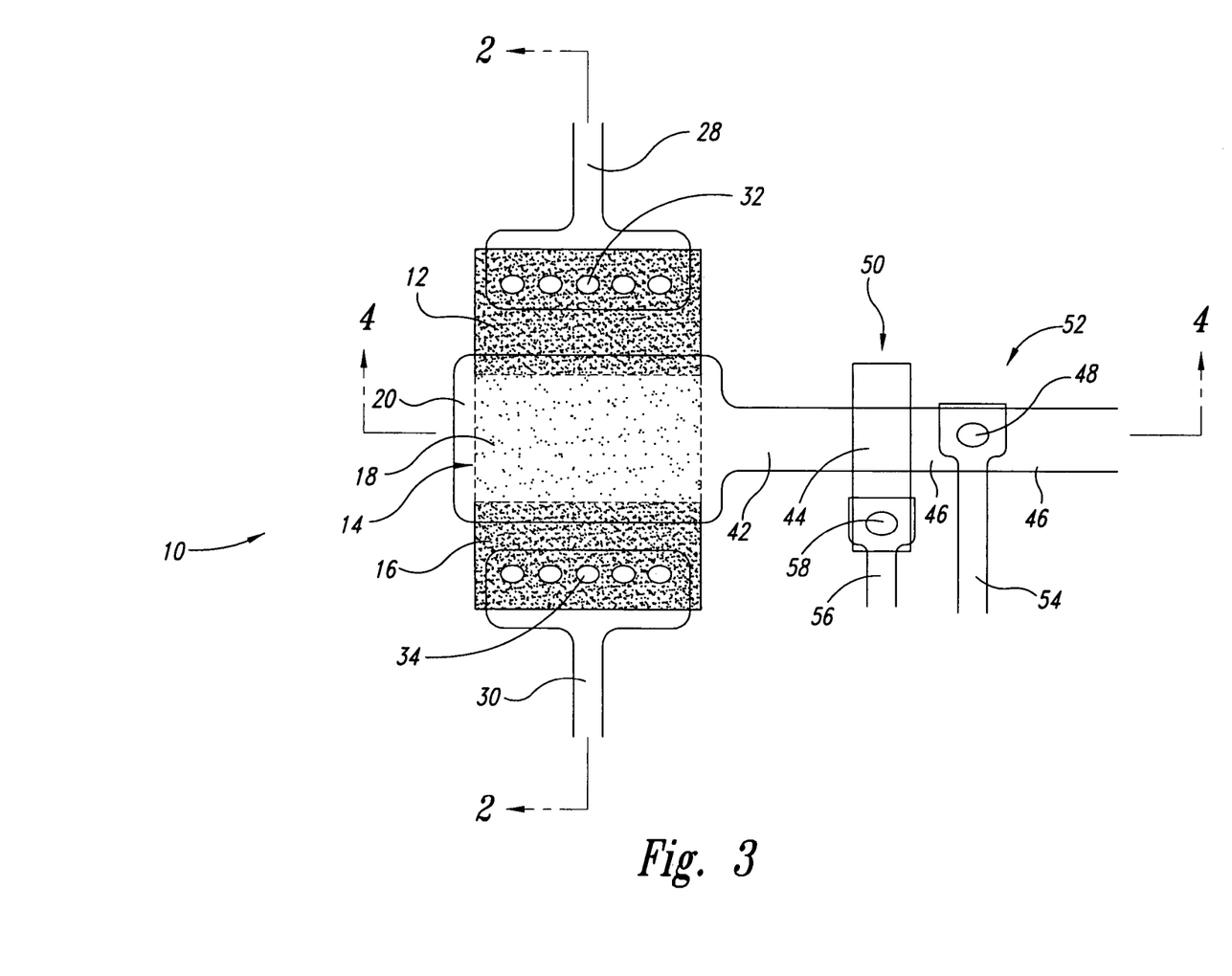
FIG. 3 is a top plan view of the heater assembly including an access transistor and a drive transistor.
Figure 4:
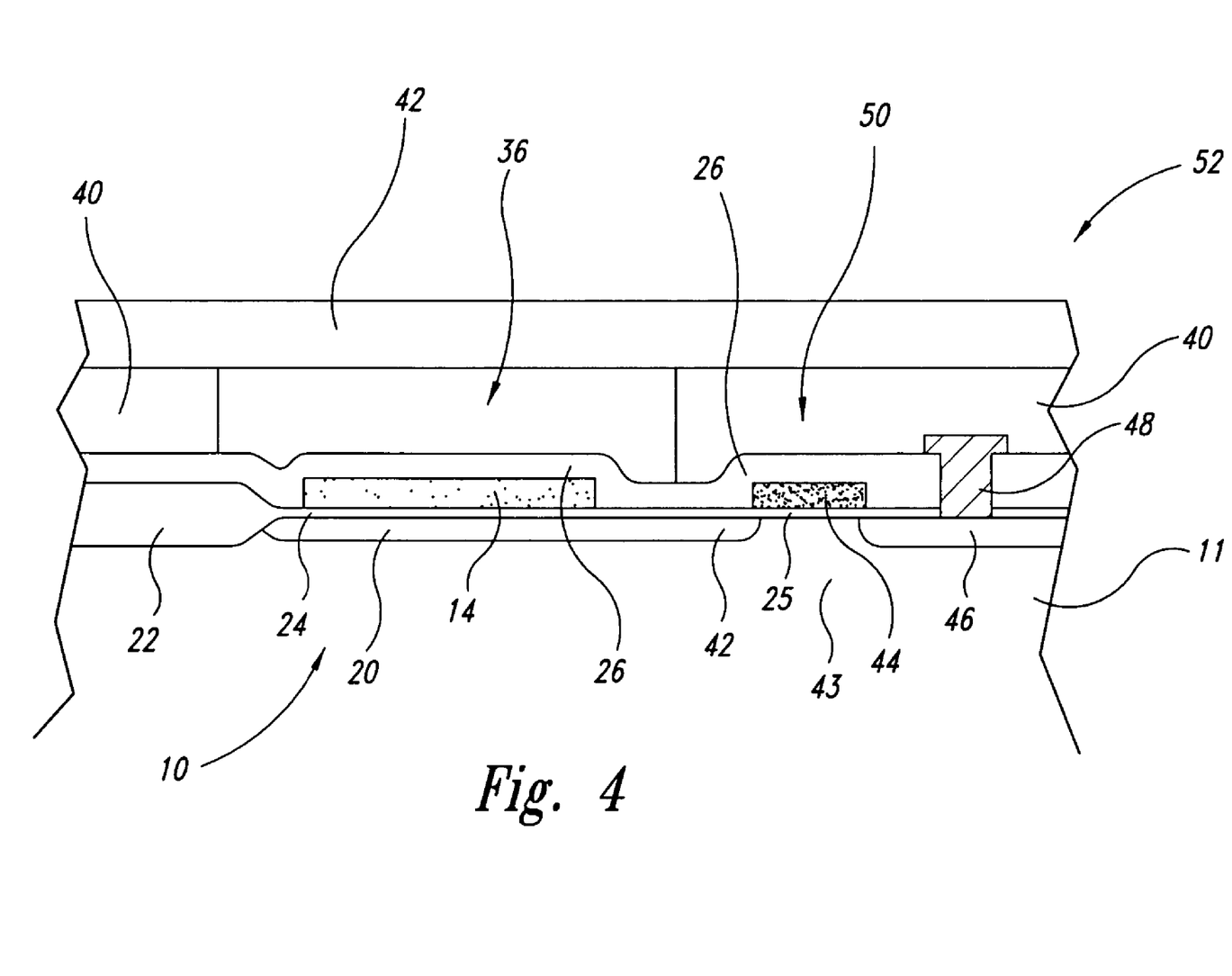
FIG. 4 is a cross-sectional view of the heater assembly taken along lines 4—4 of FIGS. 2 and 3.

FIGS. 3 and 4 illustrate further parts of the invention. The gate electrode 20 extends under the channel region 14. A logic control circuit 52 comprises a conductive region 42 connected to the gate electrode 20, the conductive region 42 being either source or drain of a pass gate transistor 50. The pass gate transistor 50 is in the form of a standard MOS transistor having a channel region 43 in the monocrystalline substrate 11 and having a drain region 46 and a source region 42. In one embodiment, gate dielectric 25 of pass gate transister 50 is the same as the gate dielectric 24 of the thin film transister 10, the layer 24 being formed in the same process step and as a contiguous, single layer from the pass gate transistor 50 and the heating transistor 10. In an alternative embodiment, the two transistors have separate thicknesses and/or different materials for the gate dielectrics 24 and 25, respectively. In many embodiments, it will be desired to have the transistors with different threshold characteristics and different turn on and turn off characteristics. One way to achieve this is to have different gate dielectrics 24 and 25. Accordingly, in some embodiments the gate dielectrics 24 and 25 will be identical for the two transistors 50 and 10 and the doping profiles of the respective gate electrodes and channels will be different. On the other hand, the gate dielectrics 24 and 25 may be different, having been formed in different steps and being of a different thickness or composed of different materials.

The MOS transistor 50 includes a drain region 46 which is electrically connected to a power supply 54 by contact 48. The contact 48 has a voltage at a desired value, for example 3 volts, 5 volts, 8 volts or any selected value that is desired to transfer to the gate electrode 20 of the thin film transistor 10. A conductive path 56 is coupled to the gate electrode 44 of the pass gate 50 at contact 58. The conduction line 56 is coupled to the appropriate control circuitry to be selectively brought high or low on a desired sequence in order to power the gate electrode 44 at the pass gate to provide the voltage to the gate 20 of the thin film transistor 10. When the gate electrode 44 is brought high then the transistor 50 is enabled, passing the voltage at drain 46 to the drain 42 and thus to the gate electrode 20. The transistor 50 in one embodiment is an n-type so that applying high voltage enables the transistor and the voltage applied can be of a standard $V_{DD}$ value or may be of an increased value such as twice a threshold value above $V_{DD}$ to pass a higher voltage. Alternatively, the pass gate transistor 50 may be a p-channel transistor so that it is enabled when the gate electrode 44 is taken low to provide the desired voltage on the gate electrode 20 of the thin film transistor.

The terms "source" and "drain" are interchangeable, depending on the current flow and type of transistor used so that in some embodiments, the source may be 46 and the drain 42. For example, during one part of the operation it may be desirable to ground the gate electrode 20 after taking it to a high voltage. In such an embodiment, the voltage on power supply line 54 will be switched from high to ground followed by enabling pass gate 50. This will remove any voltage or excess charge on the gate electrode 20, pulling it to ground via power supply line 54 which has been coupled to ground. The source being 46 and the drain being 42 in this instance of operation. Their names may also be switched for p-channel transistors, depending on the relative voltage levels between the two regions and the state of operation.

The thin film transistor 10 is enabled when the gate electrode 20 is taken to the appropriate voltage, whether high, for an n-type transistor or low, for a p-channel transistor. A relatively high voltage is coupled to the drain 12 via power supply line 28. A plurality of contacts 32 provide a high current carrying capability from the power supply line 28 to the drain region 12. When the gate electrode 20 is taken to a high voltage, this places an electric field through the gate oxide 24 to the channel region 14, causing a current to pass from the drain 12 to the source 16 and providing a series electrical connection from power supply line 28 to line 30. A central resistive region 18 heats quickly to a high temperature when current is passed therethrough. The heat reaction chamber 36 is heated by the resistor member 18 to the desired level. The amount of current and the timing for such current passing through the thin film transistor 10 is precisely controlled by the gate electrode 20 so as to provide a desired amount of heating of the heat reaction chamber 36.

The gate electrode 20 is a voltage-controlled device which is responsive to the voltage provided to it via pass gate 50. There is little, to no current consumption by the gate electrode 20 since it is an insulated gate device. Accordingly, the response time of the transistor is very quick since there is very little, to no current flow and the transistor is designed to have a fast response time with a low parasitic capacitance. This provides for fine tune control of the timing, and the amount of current via the thin film transistor 10 via the control logic as driven by the pass gate and the voltage level on power supply line 54. The actual controlling terminal 20, is therefore not a current carrying device but rather is a voltage controlled switch having significant advantages over the ohmic resistors of the prior art.

Figure 5:
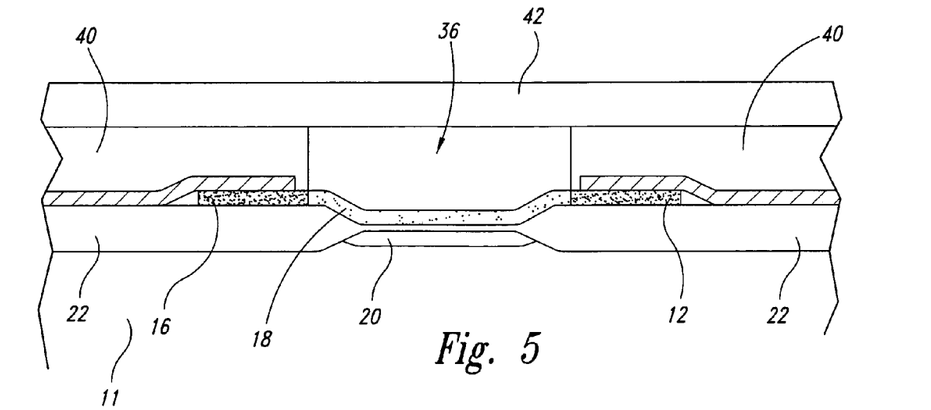
FIG. 5 is a cross-sectional view of an alternative embodiment of the heater assembly.

FIG. 5 illustrates an alternative embodiment according to principles of the present invention. In the embodiment of FIG. 5, the resistive region 18 is coextensive with the heat reaction chamber 36. The heavily doped drain 12 and source 16 are entirely outside of the heat reaction chamber 36. The highly resistive region 18 is coextensive with the bottom of the heat reaction chamber and significantly larger than the channel region 14 itself. In this instance, the turn on characteristics of the transistor are drastically altered so that somewhat higher voltage levels in the gate electrode 20 are required in order to induce conduction. Once the thin film transistor 10 is enabled, the same current flows from the drain to the source through the entire resistive region providing an even heating across the entire bottom of the resistive region. This may be advantageous in some embodiments. Further in the alternative embodiment of FIG. 5 the passivation layer 26 is not used. In some embodiments, the material within the heat reaction chamber will not cause degradation of the resistor 18 or, it may be desired to have the resistive element 18 in direct contact with the material in the heat reaction chamber 36. For those embodiments, the passivation layer 26 is not used.

Figure 6:
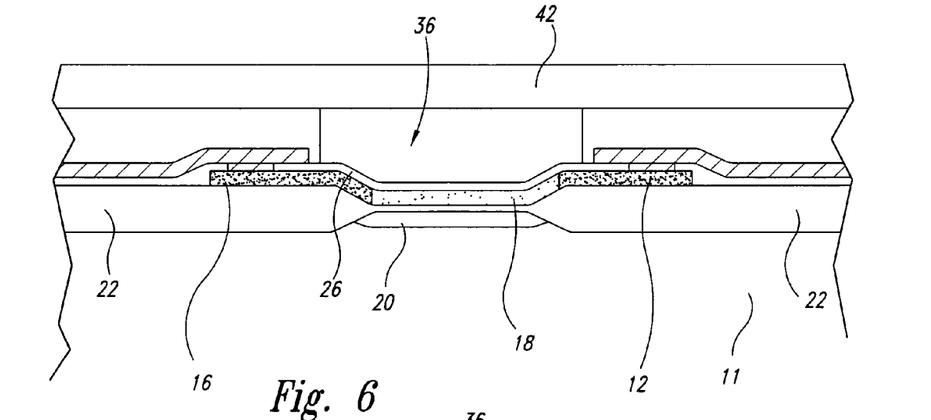
FIG. 6 is a cross-sectional view of a further alternative embodiment of the heater assembly.

FIG. 6 illustrates an alternative embodiment in which the thin film transistor 10 has a drain offset to minimize the $I_{OFF}$ current. The embodiment of FIG. 6 is preferred in many designs where a precise control of the thin film transistor 10 is desired while still maintaining sufficiently rapid turn on characteristics.

Figure 7:
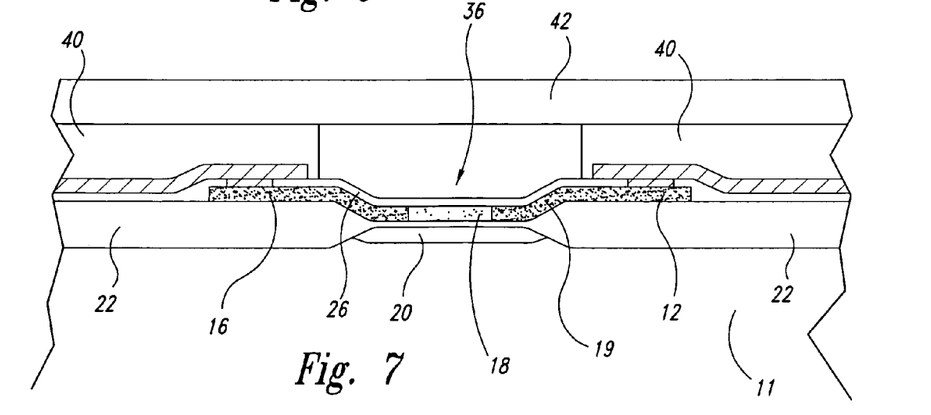
FIG. 7 is a cross-sectional view of a further alternative embodiment of the heater assembly.
Figure 8:
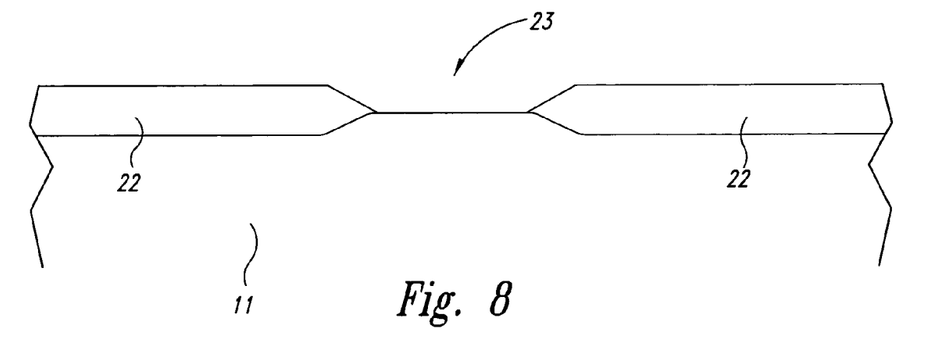
FIGS. 8–12 illustrate the steps carried out to form the device of the present invention.

FIG. 7 shows an alternative embodiment in which the resistive region 18 is significantly smaller than the gate electrode 20. In this embodiment, the resistive region 18 is a relatively small strip, and the gate electrode 20 extends substantially on either side of the highly resistive region 18. The length of the channel may therefore be selectively chosen to provide a desired heating characteristic coupled with the desired turn on characteristics and speed to heat the reaction chamber 36 at a desired rate.

A transistor designed according to the embodiment of FIG. 7 will therefore have very fast turn on characteristics and can provide a much higher current density for a given area at a more rapid rate than the other embodiments.

The size and location of the reaction chamber 36 may be selected according to a desired end use and positioned relative to the resistive region 18. The resistor 18 may be located in the various positions as shown in FIGS. 2–7 being generally centrally located with respect to the heat reaction chamber 36 and having a desired width relative to the chamber itself. Alternatively, the chamber 36 may be made of such a size to exactly equal the channel region itself or the gate electrode 20. For example, in the embodiment of FIG. 7 the reaction chamber 36 may be exactly equal to the size of the resistive region 18 if desired. This could be done easily by using the same mask dimensions for both the resistive region 18 and the channel region 36. It can also be made smaller by having a relatively larger gate electrode and resistive area.

FIGS. 8–11 illustrate the process steps to be carried out in constructing a device according to the present invention. Beginning with a silicon substrate 11, isolation layers 22 are formed which provides an active area 23 where the isolation regions 22 are not present. The isolation regions 22 may be trench isolation, a trench or recess that is filled with oxide, standard field oxide or any acceptable isolation structure so as to create the active areas of the size and type shown, such structure being well known in the art. Following the formation of the active areas, the gate dielectric 25 is formed. In one embodiment, a single gate dielectric is formed which extends under both the pass gate 50 and the thin film transistor 10. Alternatively, the gate dielectric 25 is formed at this stage from selected materials and the gate dielectric 24 is later formed from different materials for the thin film transistor 10. Following the formation of the appropriate gate dielectric 25, a blanket polysilicon deposition is performed with masking and etching to create the gate electrode 44 for the pass transistor 50. The gate electrode 44 is thereafter heavily doped so as to be conductive while at the same time forming the source and drain regions 46 and 42 of the pass transistor and the gate electrode 20 of the thin film transistor. This doping can be carried out with the active area entirely exposed or covered with a sacrificial pad oxide as is known in the art. In the event the same gate dielectric 24 is used for both transistors, the implant energy into the gate electrode region 20 will be sufficiently high to pass completely through the gate dielectric 24. In the alternative embodiment in which separate gate electrodes are used, the gate electrode 20 will not have a gate dielectric thereon. The implant is therefore made into the substrate directly or through the sacrificial pad oxide which is later removed. The gate electrode 20 is therefore preferably formed simultaneously by the implant forming the source and drain region 42 and 46 of the pass transistor 50. Other active transistors that are part of the logic control circuit 52 will also be formed at the time and in the same process steps as transistor 50.

Figure 9:
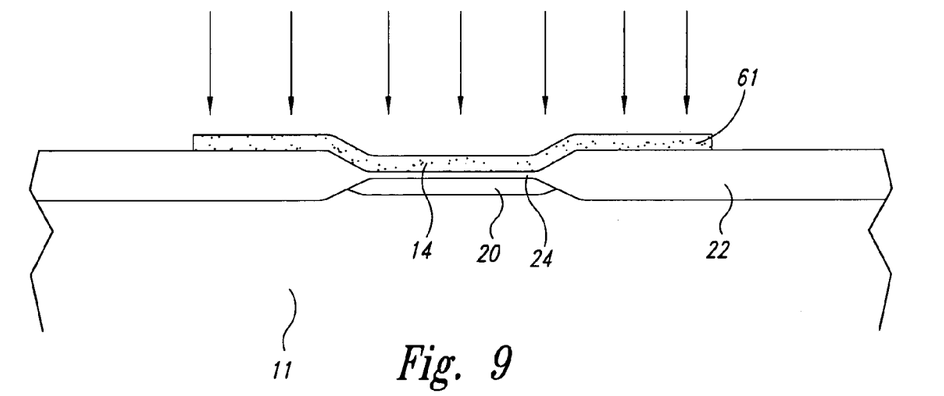
Figure 10:
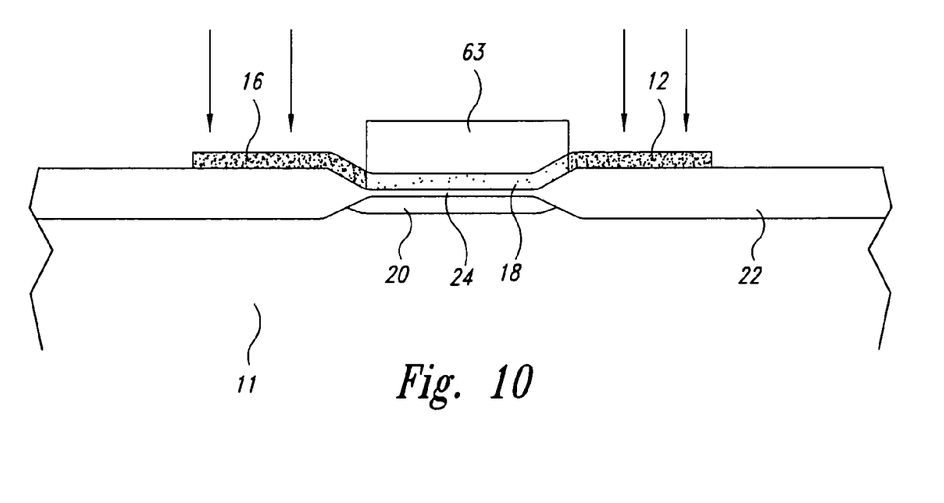

The thin film transistor 10 thereafter has the gate dielectric 24 formed thereon, either by growing or depositing an oxide layer or deposition of the appropriate nitride layer and oxide sandwich depending on the type of gate dielectric 24 desired for the thin film transistor 10. A second polysilicon deposition is now performed for the thin film transistor to form the contiguous polysilicon layer 61 which will become the drain 12, channel 14 and source 16 of the thin film transistor 10. FIG. 9 illustrates the process carried out sufficient that the polysilicon layer 61 for the thin film transistor 10 has been deposited. According to one embodiment, the appropriate channel threshold and resistor doping is provided into the polysilicon layer 61 as shown in FIG. 9 to dope the material for the highly resistive region 18 and the appropriate channel threshold voltage. In some instances, the doping may be p-type while in other embodiments the doping is n-type. In one embodiment, no doping takes place and undoped polysilicon is used for the highly resistive region 18 and for the channel 14. Following the resistor implant, if used, for the resistor 18 in FIG. 9, a mask 63 is placed over the resistor region 18 as shown in FIG. 10. The heavy doped implant is then provided into the exposed polysilicon to form the drain 12 and the source 16. The dopant may be opposite that of the channel dopant of the previous step and be of sufficiently high dose to counter dope the polysilicon. Alternatively, it may be of the same conductivity type as the channel since the transistor channel is in polysilicon and such transistors have distinctive turn-on characteristics as described in many publications well known in the prior art, depending on the type of transistor to be formed.

After the source and drain regions are formed, the blocking mask layer 63 is removed by the appropriate etching and a passivation layer 26 is formed over the polysilicon layer 61. The passivation layer 26 for the heater element can be formed by anodization, oxidization, nitrodization of the channel, deposition of an oxide or nitride or any other acceptable passivation layer process. The material used for the passivation layer 26 is selected to be a material which is compatible with the heat reaction chamber materials and with any fluid which may be within the chamber. In one embodiment, no passivation layer 26 is formed, as previously shown and described with respect to FIG. 5. Following the formation of the heat passivation layer the appropriate interconnect formation layers are formed to provide the power supply layers 28 and 30 as well as the appropriate power supply lines 54 and 56 as previously described with respect to FIG. 3.

Figure 11:
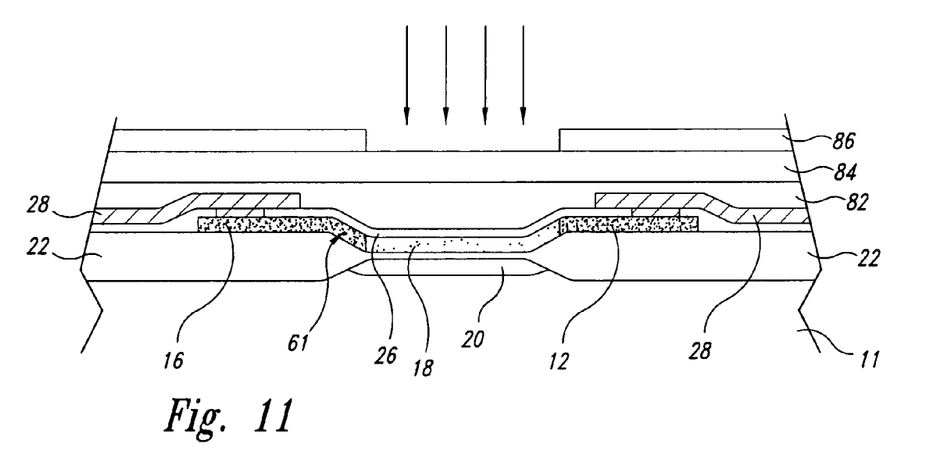

FIG. 11 shows that the heat chamber 36 is then formed by appropriate techniques. According to one embodiment, a blanket layer of an organic polymer, such as a photosensitive polymer or SU8 is deposited over the entire substrate. Cavities are formed within the organic polymer by adjusting the focus depth of a light source to expose only lower portions, below the top surface. In this embodiment, the interior portions of the organic polymer are exposed to light whereas the top portion over the heat reaction chamber 36 is not exposed to light. The inlet and outlet pass into the chamber 36 may also be formed at this time by appropriate focus of the light at the locations where the inlet and outlet to the fluid chamber 36 are desired to be formed. The formation and location of the inlet and outlet to such as fluid chamber may be of a conventional size shape and location as is known in the art. An acceptable location is described in currently pending application Ser. Nos. 09/874,382 and 09/965,128. Alternatively, the heat reaction chamber may be formed by the techniques taught in these two copending patent applications, both of which are incorporated herein by reference.

According to one embodiment, the heat reaction chamber is formed from two separate materials. A first material such as a photosensitive organic polymer 82 is deposited. On top of this, blanket layer 84 is formed, of a second material which has different etch characteristics and may have different photosensitivity than the first layer 82. The upper layer 84 is covered with a mask layer 86 and then appropriately masked and etched in order to provide the inlet and outlet chambers. The mask 86 is placed over the upper layer 84 and light is exposed through the mask 86 and through the non-sensitive layer 84 to the photosensitive layer 82 below. The chamber material 82 is therefore exposed to light followed by a standard development, process, etch, and cure. The layer 84 is left intact as a lid over the portion which is to become the heat reaction chamber 36. The result is that a heat reaction chamber 36 is formed having a top thereon with the appropriate inlets and outlets. The inlets and outlets may be on the side or bottom using techniques known in the art.

Figure 12:
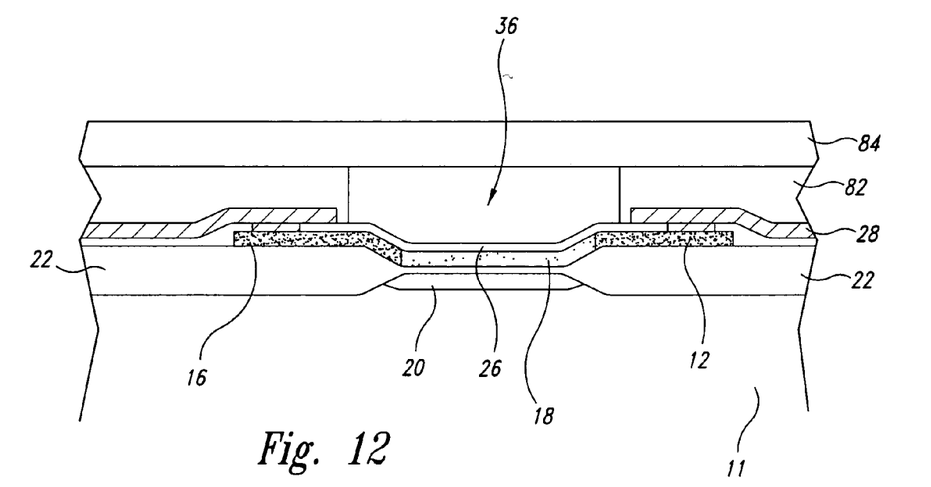

FIG. 12 shows the final heat reaction chamber with the transistor acting as the resistor in the bottom portion thereof.

From the foregoing it will be appreciated that, although specific embodiments of the invention have been described herein for purposes of illustration, various modifications may be made without deviating from the spirit and scope of the invention. Accordingly, the invention is not limited except as by the appended claims.

I claim:

1. A method of making a semiconductor heater assembly, comprising:
    forming electrically insulating regions within a semiconductor substrate;
    forming a gate electrode of a transistor within the semiconductor substrate;
    forming a gate dielectric over the gate electrode;
    forming source, drain, and channel regions of the transistor with the channel region positioned over the gate dielectric; and
    forming a microreaction chamber over the channel region of the transistor.

2. The method of claim 1, comprising:
    Forming, in the substrate, a pass transistor having a conduction terminal in electrical contact with the gate, the pass transistor configured to regulate heat-generating current in the channel region of the transistor.

3. The method of claim 1 wherein forming the microreaction chamber comprises:
    depositing a photoreactive layer over the channel region;
    depositing an additional layer on the photoreactive layer; and
    exposing the photoreactive layer to light to define the microreaction chamber.

4. The method of claim 3 wherein the exposing step is performed after depositing the additional layer.

5. A method of making a semiconductor heater assembly, comprising:
    forming electrically insulating regions within a semiconductor substrate;
    forming a gate electrode within the semiconductor substrate;
    forming a gate dielectric over the gate electrode and located between the insulating regions;
    forming a layer of polycrystalline silicon overlying the insulating regions and the gate dielectric;
    doping source and drain regions within the polycrystalline silicon layer to have a selected low resistivity to obtain a thin-film transistor;
    forming a heat responsive reaction chamber over the polycrystalline silicon layer.

6. The method according to claim 5, further including:
    doping a region within the polycrystalline silicon layer to form a resistive region having a selected resistivity.

7. The method according to claim 6 wherein the resistive region is the same conductivity type as the source and drain regions within the polycrystalline silicon layer.

8. The method according to claim 6 wherein the resistive region is a different conductivity type as the source and drain regions within the polycrystalline silicon layer.

9. The method according to claim 6 wherein the resistive region is coextensive with the heat responsive reaction chamber.

10. The method according to claim 6 wherein the resistive region is smaller than the heat responsive reaction chamber.

11. The method according to claim 5, further including:
    forming source and drain regions of a pass transistor adjacent to the gate electrode simultaneously with forming the gate electrode in the substrate, using the same process steps and having the same conductivity type.

12. The method according to claim 11, further including:
    forming a second gate dielectric for the pass transistor prior to forming the gate dielectric of the thin-film transistor.

* * * * *